(12) United States Patent
Aerts et al.

(10) Patent No.: US 6,177,447 B1
(45) Date of Patent: Jan. 23, 2001

(54) DEOXYNOJIRIMYCIN DERIVATIVES AND THEIR USES AS GLUCOSYLCERAMIDASE INHIBITORS

(75) Inventors: Johannes Maria F. G. Aerts, Abcoude; Upendra Kumar Pandit, Amsterdam; Gerrit-Jan Koomen, Heiloo; Herman Steven Overkleeft, Leiden, all of (NL); Paola Vianello, San Bovio (IT)

(73) Assignee: Universiteit van Amsterdam (NL)

( * ) Notice: Under 35 U.S.C. 154(b), the term of this patent shall be extended for 0 days.

(21) Appl. No.: 09/230,005

(22) PCT Filed: Jul. 14, 1997

(86) PCT No.: PCT/NL97/00411
§ 371 Date: Apr. 30, 1999
§ 102(e) Date: Apr. 30, 1999

(87) PCT Pub. No.: WO98/02161
PCT Pub. Date: Jan. 22, 1998

(30) Foreign Application Priority Data

Jul. 15, 1996 (EP) .................................................. 96202010

(51) Int. Cl.[7] ...................... C07D 211/46; A61K 31/445
(52) U.S. Cl. ............................................ 514/319; 546/195
(58) Field of Search .................................. 546/192, 195; 514/317, 319

(56) References Cited

FOREIGN PATENT DOCUMENTS

| | | |
|---|---|---|
| 0022192A1 | 6/1980 | (EP) . |
| 0034784A1 | 2/1981 | (EP) . |
| 0193770A2 | 2/1986 | (EP) . |
| 0305012A2 | 5/1989 | (EP) . |
| 02306962 | 12/1990 | (EP) . |
| 0477160A1 | 9/1991 | (EP) . |
| 3024901A1 | 1/1982 | (NL) . |
| WO9413311 | 6/1994 | (WO) . |
| WO9522975 | 8/1995 | (WO) . |
| WO9502161 | 1/1998 | (WO) . |

OTHER PUBLICATIONS

Aerts et al, Molecular and Biochemical Abnormalities of Gaucher Disease: Chitotriosidase, a Newly Identified Biochemical Marker, Seminars of Hamatology, vol. 32, No. 3, pp. 16–13, 1995.

Kentler, Gaucher Disease: New Molecular Approaches to Diagnosis and Treatment, Science, vol. 256, pp. 794–799, May 8, 1992.

PCT Notification of Transmittal of the International Preliminary Examination Report, 1999.

Hollak et al, Rapid Publication "Marked Elevation of Plasma Chitotriosidase Activity" A Novel Hallmark of Gaucher Disease, J. of Clinical Investigation, v. 93, pp. 1288–1292, Mar. 1994.

Primary Examiner—Zinna Northington Davis
(74) Attorney, Agent, or Firm—Cooper & Dunham LLP

(57) ABSTRACT

Deoxynojirimycin derivatives containing a large hydrophobic moiety, such as cholesterol or adamantame-methanol, linked through a spacer, such as pentamethylene, to the nitrogen atom of deoxynojirimycin, and salts thereof, inhibit glucosylceramidase and may be useful in the treatment of diseases involving a ceramide-mediated signaling process, such as Gaucher disease.

7 Claims, 3 Drawing Sheets

DEOXYNOJIRIMYCIN DERIVATIVES AND THEIR USES AS GLUCOSYLCERAMIDASE INHIBITORS

This application is filed under 35 U.S.C. § 371 as a nation phase application of PCT application number PCT/NL97/00411 filed on Jul. 14, 1997.

FIELD OF THE INVENTION

This invention is in the fields of therapy and pharmaceutical compositions for the treatment of various diseases, in particular diseases characterized by elevated plasma chitotriosidase levels, such as Gaucher disease.

BACKGROUND OF THE INVENTION
CERAMIDE, A SECOND MESSENGER

In recent years the importance of ceramide as second messenger in signal transduction has been recognized. It has become clear that the signalling induced by a number of cytokines is mediated by changes in the intracellular concentration of this lipid [1,2]. For example, crucial for the transduction of the signal exerted by TNF-α (tumor necrosis factor alpha) upon binding to its receptor are local changes in ceramide concentration in specific regions, or invaginations, of the plasma membrane. Upon binding of the cytokine to its receptor, a sphingomyelinase catalyzes the conversion of sphingomyelin into phosphorylcholine and ceramide. The ceramide that is generated in this manner propagates the signal by activating specific protein kinases and phosphatases, resulting in a cellular response. FIG. 1 gives an overview of the signalling mechanism of TNF-α and other cytokines such as interferon gamma and interleukin 6.

There is now convincing experimental evidence for the role of ceramide in signalling. It has been shown that the effects of TNF-α can be experimentally mimicked by administration of a permeable ceramide with truncated fatty acyl moiety or, alternatively, by the generation of ceramide at the cell surface by the treatment of cells with a bacterial sphingomyelinase (see e.g. ref. 2).

The above described signal transduction process is most likely a highly local event, occurring near the cytokine receptor. The concentration of ceramide in the plasma membrane is believed to be very low under normal conditions. However, considerable amounts of ceramide are present in the plasma membrane as a building block in sphingomyelin. The hydrolysis of sphingomyelin would allow a considerable local change in ceramide concentration and subsequent signal propagation.

Via action of a specific transferase, ceramide can be reconverted to sphingomyelin by transfer of the phosphorylcholine moiety from phosphatidylcholine (PC), resulting in the concomitant formation of diacylglycerol. The total pathway, resulting in the netto hydrolysis of phosphatidylcholine to phosphorylcholine and diacylglycerol, is named the sphingomyelin cycle [2].

CERAMIDE AND SPHINGOLIPID METABOLISM

Obviously, not all fluctuations in intracellular ceramide concentrations are affecting signal transduction. Ceramide is extensively metabolized in cells. The lipid is synthesized at the membrane of the endoplasmic reticulum from acylCoA and sphingosine. It may be converted at the level of the Golgi apparatus into sphingomyelin, glucosylceramide and related complex gangliosides, or galactosylceramide and related globosides and sulfatides. Sphingomnyelin and glycosphingolipids are also catabolized into ceramide and other components in the lysosomal compartment of cells. The intralysosomally formed ceramide may be locally hydrolyzed into sphingosine and fatty acid by the action of the lysosomal ceramidase or it may be exported to the cytosol and re-used for synthesis of sphingolipids. A schematic overview of the ceramide metabolism is presented in FIG. 2.

SPHINGOLIPIDOSES: GAUCHER DISEASE

In man a number of inherited disorders in lysosomal sphingolipid catabolism occur, the so called sphingolipidoses (see Table 1). For example, an inherited deficiency of the lysosomal sphingomyelinase underlies Niemann-Pick disease, and defective activity of the lysosomal ceramidase causes Farber disease. The most frequently encountered sphingolipidosis is Gaucher disease [3]. The metabolic basis of this disorder is a deficiency of the lysosomal beta-glucosidase, glucocerebrosidase (E.C.3.2.1.45). This enzyme catalyzes the hydrolysis of glucosylceramide (glucocerebroside) to glucose and ceramide. In patients with Gaucher disease glucosylceramide accumulates in tubular aggregates, in particular in lysosomes of macrophages. The lipid-laden macrophages have a typical morphology and are usually referred to as 'Gaucher cells'. In the course of clinical manifestation of Gaucher disease the abnormal macrophages may accumulate in large quantities in various body locations, such as the bone marrow compartment, spleen, liver, kidney, and lungs. The most pronounced clinical symptoms associated with Gaucher disease are progressive splenomegaly, hepatomegaly, and skeletal deterioration. Most Gaucher disease patients do not develop neurological complications. The common non-neuronopathic form of the disease is called Type 1 Gaucher disease. In very severe cases of Gaucher disease characteristic neurological abnormalities may also occur, resulting in lethal complications at infantile (Type 2) or juvenile (Type 3) age [3].

GAUCHER CELLS

The glucosylceramide-laden Gaucher cells are believed to play a crucial role in the pathophysiology. Their massive presence in various body locations is thought to lead to local pathology.

Gaucher cells should not be viewed as inert containers of glycosphingolipid. The storage cells are viable and actually, being activated macrophages, secrete large amounts of specific proteins such as hydrolases and cytokines. These factors in turn act as pathogenetic agents that cause local tissue damage and turnover. Moreover, Gaucher-cell derived factors such as cytokines promote the recruitment of additional activated macrophages (see FIG. 3 for a schematic overview).

Recently a sensitive marker for Gaucher cells has been discovered by us [4]. Using the technique of in situ hybridization we observed that Gaucher cells synthesize large quantities of the secretory enzyme chitotriosidase, the human analogue of chitinases present in various species. This explains the dramatic elevation in plasma chitotriosidase levels in clinically affected Gaucher patients. On the average chitotriosidase levels are about 1000 fold higher in plasma of these patients as compared to corresponding normal subjects. In presymptomatic or asymptomatic individuals with an inherited glucocerebrosidase deficiency plasma chitotriosidase levels are (almost) within the normal range (see Table 2). Interestingly, elevated levels of plasma chitotriosidase have also been noted for patients with other sphingolipidoses, in particular Niemann-Pick disease [5].

It has been observed that in cultured macrophages, derived from peripheral blood monocytes, the concentration of glucosylceramide gradually increases. The increase in glycolipid is more pronounced when cells are grown in the presence of conduritol B-epoxide, a potent irreversible inhibitor of glucocerebrosidase. After approximately 7 days of culture the macrophages start to produce chitotriosidase mRNA and secrete the enzyme [4,6]. The expression of the chitotriosidase gene subsequently dramatically increases: after about three weeks chitotriosidase constitutes almost 1% of the total synthesized protein, as revealed by the incorporation of radioactively labeled methionine [7]. The continuous presence in the culture medium of glucosylceramide, or of conduritol B-epoxide (an irreversible inhibitor of lysosomal glucocerebrosidase), promotes chitotriosidase expression.

THERAPEUTIC INTERVENTION FOR GAUCHER DISEASE

The sparse and anecdotal information on the natural history of Gaucher disease indicates that although clinical symptoms develop progressively, the disease manifestation is usually not a gradual proces. In the case of most patients abnormalities develop rapidly at a particular age in a specific tissue, may subsequently stabilize for considerable time, to become next rapidly progressive again. In other words, disease progression has a local and chaotic feature. Most likely, Gaucher cells play a critical role in these local pathogenetic processes. The presence of the activated storage cells will locally induce tissue damage and turnover, and promote recruitment of activated macrophages at these sites, initiating a chaotic cascade of pathological events (see FIG. 3). According to this concept, a major beneficial effect should be exerted by a disruption or prevention of the pathological cascade. The various therapeutic approaches for Gaucher disease that have been considered are discussed here below.

ENZYME SUPPLEMENTATION THERAPY

For more than thirty years supplementation of macrophages of Gaucher patients with human glucocerebrosidase has been seriously considered as a therapeutic option. Efforts to develop a therapy for Gaucher disease have been largely unsuccessful for many years due to the unavailability of sufficient amounts of pure human glucocerebrosidase and the poor targeting of intravenously administered enzyme to lysosomes of tissue macrophages. Only since 1990 an effective therapeutic intervention for Gaucher disease is available that is based on the chronic supplementation of patients with human glucocerebrosidase [8]. Administered by intravenous infusion is a human glucocerebrosidase that is modified in its N-linked glycans such that mannose-residues are terminally exposed. The modification favours uptake via mannose receptors. Improved targeting of the modified ('mannose-terminated') enzyme to lysosomes of tissue macrophages occurs via mannose-receptor mediated endocytosis. Different dosing regimens that vary with respect to total dose (15–240 U/kg body weight.month) and frequency of administration (three times weekly to biweekly) are presently used (see e.g. ref. 9). Glucocerebrosidase isolated from human placenta (Ceredase; alglucerase) and enzyme recombinantly produced in CHO-cells (Cerezyme; imiglucerase) have been found to be equally potent in reversing some of the clinical signs associated with the disease [10].

The most pronounced beneficial effects of enzyme replacement therapy are the reductions in liver and spleen volumes, and the improvements in hematological parameters such as hemoglobulin concentration and thrombocyte and leukocyte counts. Marked interindividual differences exist in the rate and extent of clinical response, even among related patients that are treated with the same dosing regimen [9]. In general, the most marked clinical improvements occur within the first year of treatment, accompanied by a pronounced correction of biochemical serum abnormalities. A complete reversal of clinical signs and complete normalization of serum abnormalities, such as elevated levels of angiotensin converting enzyme, tartrate-resistant acid phosphatase and chitotriosidase, is not accomplished by enzyme therapy, not even in the case of patients that receive a high dose of glucocerebrosidase for a number of years [11]. The partial correction following enzyme therapy is in contrast to the complete correction that is noted for patients that underwent a successful bone marrow transplantation.

Conflicting views still exist with respect to the optimal dosing regimen for enzyme therapy. Whereas low dosing regimens may be (almost) equally successful to high dosing regimens in generating hematological improvements, this is still questionable with respect to intervention of the bone disease.

Presently more than 1500 patients are receiving enzyme therapy. This recent development has attracted considerable scientific and public attention, also due to the high costs and potential risks that are involved. The costs associated with successful therapy have hitherto been exceptionally high ($100,000 to $400,000 annually per patient); leading to the belief that the enzyme therapy of Gaucher disease is the most expensive drug treatment for any disease. Although the alglucerase preparation is known to contain minor amounts of HCG and other impurities, the experience so far indicates that enzyme therapy is safe.

The enzyme therapy for Gaucher disease is considered to be a model case for the future development of treatments for other rare genetic disorders—a point perhaps best illustrated by the organisation in February/March 1995 of a Technology Assessment Conference at the National Institutes of Health, Bethesda, USA, that was specifically devoted to Gaucher disease. This type of conference is only organised when there is an exceptionally pressing health care need. During the conduct of the conference, a panel of 12 independent experts took evidence from leading scientists and clinicians in the field of Gaucher disease; the panel concluded that enzyme therapy is effective in reversing a number of clinical signs associated with Gaucher disease. Furthermore, it was stressed that reduction of the costs and the associated potential risks of human protein replacement therapy are critical issues both from the point of view of patient care and health care economics [12].

OTHER THERAPEUTIC APPROACHES

A successful treatment of Gaucher disease by bone marrow transplantation has been accomplished for a limited number of juvenile Gaucher patients. The introduction of the normal genetic information for glucocerebrosidase in hematopoietic stem cells results in the formation of blood cells that are able to hydrolyze glucosylceramide at normal rates. The fact that clinical abnormalities disappear in Gaucher patients following a successful bone marrow transplantation indicates that the presence of blood cells with normal glucocerebrosidase activity is sufficient for prevention of disease symptoms. Unfortunately, the applicability of bone marrow transplantation as treatment for Gaucher disease is quite restricted due to the limited availability of bone marrow from matched donors and the considerable morbidity associated with this intervention, particularly in the case of adults.

In recent years the option of gene therapy of Gaucher disease is intensively studied. In general, the following approach is envisioned. Pluripotent hematopoietic stem cells are isolated and transduced with a vector containing human glucocerebrosidase cDNA. After successful transduction the stem cells are re-introduced in the patient. Although data obtained with animal studies suggest that Gaucher disease is an attractive candidate for gene therapy, a number of serious problems still have to be solved before efficient intervention in this manner can be expected. A major disadvantage is that the 'genetically corrected' stem cells and their progeny most likely have no selective advantage. It is therefore assumed that in order to be effective gene therapy has to result in a stable correction of a major proportion of the pluripotent stem cells. For a critical evaluation of the state of the art concerning gene therapy see ref. 13.

A distinct therapeutic approach that has been proposed for Gaucher disease is the so called 'substrate deprevation therapy' [14–16]. It is argued that a marked reduction of the synthesis of glucosylceramide may have a beneficial effect because the amount of glucosylceramide that has to be degraded by macrophages would be lower. Several inhibitors of glucosylceramide synthase have been developed, e.g. 1-phenyl-decanoylamino-3-morpholino-1-propanol (PDMP) and its analogue 1-phenyl-2-hexadecanoylamino-3-morpholino-1-propanol (PPMP) [14], butyl-deoxynojirimycin [15] and butyl-deoxygalactonojirimycin [16].

A disadvantage of the 'substrate deprevation' approach is that a priori not only the synthesis of glucosylceramide but also that of more complex glycosphingolipids is inhibited. Moreover, the presently available inhibitors of glucosylceramide synthase are known to exert a number of important biological effects that may limit their applicability as therapeutic agent. For example, PDMP is known to induce apoptosis in some cell types. Butyl-deoxynojirimycin is known to inhibit also the lysosomal glucocerebrosidase and the a-glucosidase I, an ER enzyme that plays a critical role in trimming of N-linked glycans in newly formed glycoproteins and as such in quality control of protein folding. The antiviral action of butyl-deoxynojirimycin is thought to be caused by its inhibitory effect on glycoprotein modification. Moreover, it was recently reported that glucosylceramide synthase inhibitors induce the synthesis of the enzyme. Consequently, these inhibitors would need to be chronically administered to Gaucher patients since their withdrawal would be followed by an abnormally high level of glucosylceramide synthase activity and increased load on glucosylceramide [14].

SUMMARY OF THE INVENTION

This invention provides a deoxynojirimycin derivative containing a large hydrophobic moiety linked through a spacer to the nitrogen atom of deoxynojirimycin, and salts thereof.

The word 'spacer' refers to any bivalent moiety or group capable of linking a hydrophobic group to the N atom of deoxynojirimycin. Said spacer preferably comprises a polyalkylene chain of from 3 to 8 carbon atoms, more preferably 3 to 6 carbon atoms, most preferably 5 carbon atoms. In a particularly preferred embodiment of the invention, the spacer consists of a group having the structure —$(CH_2)_n$— wherein n is an integer from 3 to 8, preferably 3 to 6, most preferably 5.

The phrase 'large hydrophobic moiety' refers to any hydrophobic group or moiety that has a lipophilic nature and tends to stably insert in biological lipid-bilayer membranes. Normally it comprises at least one saturated, unsaturated or partially unsaturated cyclic structure, in particular a condensed ring structure comprising two or more condensed rings. More preferably, the large hydrophobic moiety is derived from a polycyclic alcohol containing three or more rings each sharing two or more carbon atoms with another ring. The large hydrophobic moiety has the ability to insert in lipid bilayers.

Preferably said large hydrophobic moiety is derived from a compound selected from the group consisting of adamantanemethanol, cholesterol, β-cholestanol, adamantanol and 9-hydroxyphenanthrene.

This invention furthermore provides a pharmaceutical composition containing such deoxynojirimycin derivative, and a variety of applications of said deoxynojirimycin derivative, including several therapeutical uses.

DETAILED DESCRIPTION OF THE INVENTION

A NOVEL THERAPEUTIC APPROACH: INHIBITION OF MACROPHAGE ACTIVATION

Currently enormous costs are associated with enzyme therapy and the efficacy of this approach proves to be intra-individually highly variable. The present alternatives for therapeutic intervention either can be applied only for a limited number of cases (bone marrow transplantation), or have in fact not yet been shown to be effective and safe (gene therapy and substrate deprevation). This has prompted us to search for a novel option for therapeutic intervention that may be used in addition to enzyme therapy.

Figure 3:
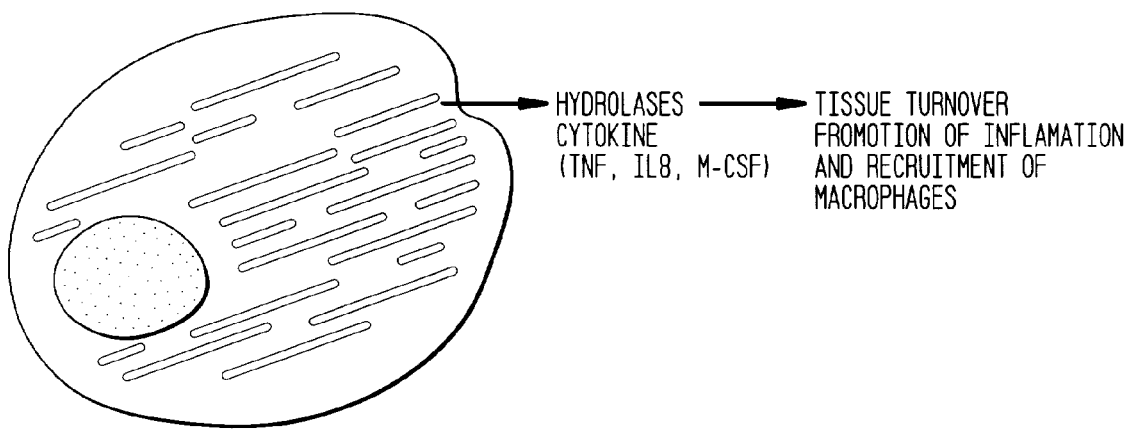
FIG. 3 depicts the pathophysiology of Gaucher disease. Lipid-laden macrophages ('Gaucher cells') secrete hydrolases and cytokines that cause tissue damage and turnover and that promote recruitment of macrophages, thus causing a pathological cascade.

According to our view on the pathogenesis of Gaucher disease (see FIG. 3), the activation of macrophages that leads to the release of hydrolases and cytokines forms an ideal target for intervention.

An agent that is capable of preventing the activation of Gaucher cells should have a therapeutic value, and moreover should be able to augment the efficacy of enzyme therapy.
THE DEVELOPMENT OF AN INTERVENTION BASED ON INHIBITION OF MACROPHAGE ACTIVATION
IDENTIFICATION OF THE TARGET FOR INTERVENTION In order to be able to develop the desired therapeutic agent, first the mechanism by which Gaucher cells are driven in their characteristic activated state had to be elucidated.

Two crucial findings were made by us in the course of our investigations that allowed us to develop the envisioned agent.

In the first place, we discovered a sensitive marker for the characteristic activated state of Gaucher cells, i.e. the massive synthesis and secretion of chitotriosidase by these cells (see above). Importantly, the potential of agents to prevent the relevant activation of macrophages can be sensitively tested by the analysis of their capacity to inhibit the production and secretion of chitotriosidase by macrophages in cell culture.

In the second place, we discovered that human cells contain, besides the lysosomal glucocerebrosidase, a distinct enzyme that is capable of hydrolyzing glucosylceramide into glucose and ceramide [17].

NON-LYSOSOMAL GLUCOSYLCERAMIDASE

The glucosylceramidase differs in many respects from the lysosomal glucocerebrosidase. The enzyme is not located in lysosomes in contrast to glucocerebrosidase; it is not deficient in Gaucher disease in contrast to glucocerebrosidase; it behaves as an integral membrane protein whilst glucocerebrosidase shows the features of a membrane-associated protein; and finally, it differs from glucocerebrosidase in specificity towards artificial substrates, inhibitors and activators. For example, the glucosylceramidase is not able to hydrolyze artificial b-xylosidic substrates contrary to glucocerebrosidase. Glucocerebrosidase is irreversibly inhibitable by conduritol B-epoxide in contrast to the glucosylceramidase that is insensitive for this compound. The lysosomal activator protein saposin C potently stimulates glucocerebrosidase in its enzymatic activity but is without effect on the glucosylceramidase.

Concerning the function of glucosylceramidase, an important observation was made. Using a relatively novel technique for subcellular fractionation it was found that the glucosylceramidase is present at the plasma membrane or in early endosomal structures. In other words, the enzymatic activity of the glucosylceramidase results in the generation of ceramide in the plasma membrane or specific invaginations of this membrane. It is known that significant amounts of glucosylceramide are indeed present in the plasma membrane. Consequently the activity of glucosylceramidase might result in relevant changes in ceramide concentration in those cellular membranes that are involved in ceramide-mediated signalling.

It was furthermore observed using membrane suspensions prepared from cells and tissues that the ceramide formed from glucosylceramide by the activity of the lysosomal glucocerebrosidase is hardly converted into sphingomyelin; in sharp contrast to this is the efficient conversion of the ceramide formed by the action of glucosylceramidase into sphingomyelin. Apparently, the ceramide generated by the glucosylceramidase activity is rapidly further metabolized within the same membranes, as can be expected for a lipid that acts as transient second messenger.

Figure 4:
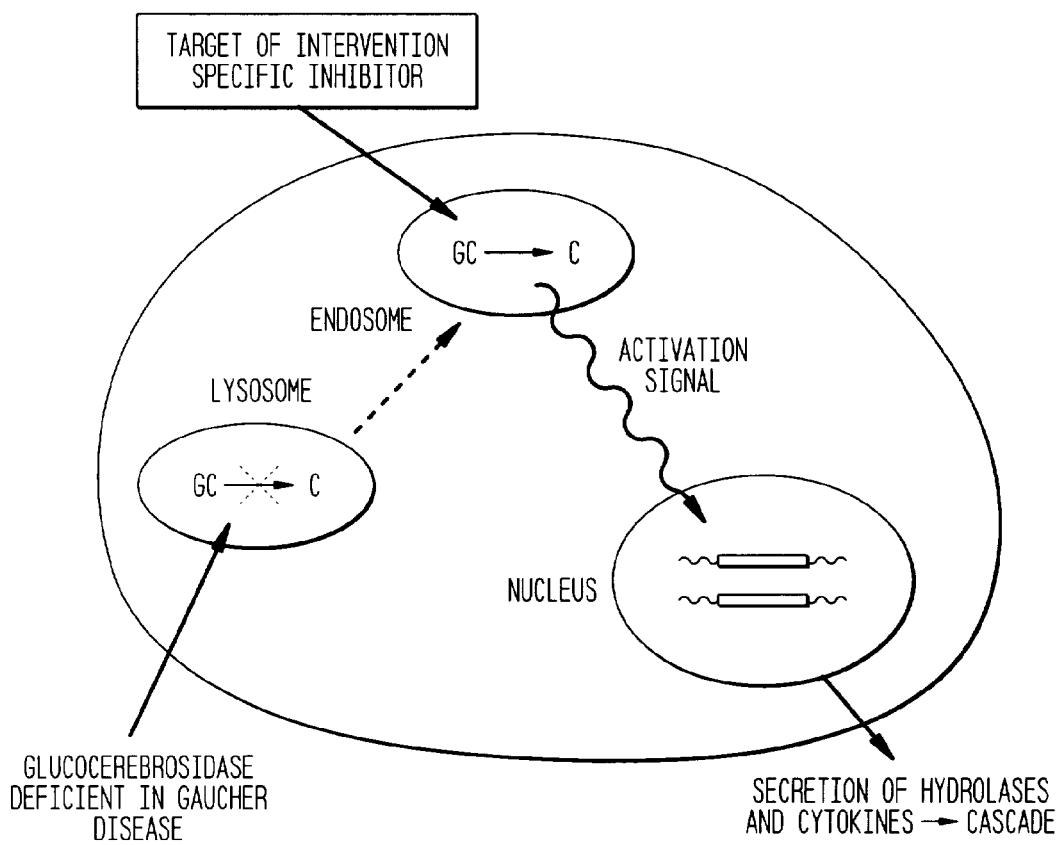
FIG. 4 presents a hypothetical model for the pathogenesis of Gaucher disease and a target for intervention. Due to lysosomal impairment of GC (glucosylceramide) catabolism in the lysosomes the activity of the non-lysosomal glucosylceramidase is increased. This results in increased ceramide (C) production and associated therewith signalling to the nucleus. This leads to production and secretion of specific factors that propagate the pathological cascade. Intervention in the pathogenetic mechanism should be feasible by specifically inhibiting the activity of glucosylceramidase.

On the basis of these findings we postulate a new mechanism for the pathological activation of macrophages in Gaucher disease. In this model, as depictured in FIG. 4, it is proposed that the lysosomal impairment to degrade glucosylceramide in glucocerebrosidase-deficient individuals also leads to an increased concentration of this glycolipid in membranes containing the glucosylceramidase. Consequently, the glycolipid is there at an abnormal high rate hydrolysed to ceramide. This ceramide activates protein kinases and phosphatases, resulting in the characteristic activation of the macrophage and the corresponding production and release of pathogenetic factors. Experimental proof for this model in which the constitutively stimulated glucosylceramidase activity promotes macrophage activation is described below.

GLUCOSYLCERAMIDASE ACTIVITY AS TARGET FOR THERAPEUTIC INTERVENTION

The glucosylceramidase is an ideal and novel target for prevention of the activation of macrophages in Gaucher disease. Specific inhibition of the enzyme activity would prevent further release of pathogenetic factors and disrupt the pathological cascade, resulting in a therapeutic effect. It may be envisioned that the combination of this approach with that of enzyme supplementation can improve markedly the efficacy of therapeutic intervention and meanwhile will result in a significant reduction of associated costs.

DESIGN OF A SPECIFIC INHIBITOR FOR GLUCOSYL-CERAMIDASE ACTIVITY

The properties of the glucosylceramidase present in membrane suspensions and intact cells were carefully analysed in order to identify a suitable inhibitor for the enzyme. A number of important findings were made in this connection.

It was observed that the enzyme is tightly integrated in the membrane and most likely hydrolyzes its substrate glucosylceramide while this is also inserted in the membrane. The identification of the location of the glucosylceramidase in (invaginations of) the plasma membrane is also of importance.

Furthermore, a number of known glucosidase inhibitors (D-gluconolacton, castanospermine, deoxynojirimycin and butyl-deoxynojirimycin) were tested on their capacity to inhibit the glucosylceramidase activity. The most promising inhibitors were deoxynojirimycin and in particular butyl-deoxynojirimycin. However their specificity as well as that of the other inhibitors tested was poor. For example, the lysosomal glucocerebrosidase is also quite sensitive to the inhibitors, rendering them unattractive for administration to the already glucocerebrosidase-deficient Gaucher patients. The inhibitors would moreover seriously interfere with enzyme therapy of patients due to their inhibitory effect on the administered alglucerase or imiglucerase.

It was noted that incubation of intact cells with deoxynojirimycin or butyl-deoxynojirimycin at their IC50 concentration for glucosylceramidase (20 and 0.3 uM, respectively), resulted also in a significant inhibition of glucocerebrosidase activity (about 20 and 10%, resp.) and in an inhibition of glucosylceramide synthase activity (about 30 and 20%, respectively). In the same concentration range a marked inhibition of ER a-glucosidase I activity (N-linked glycan trimming) has also been reported for several cell types [15].

The negative results with known glucosidase inhibitors prompted us to design a novel, more specific inhibitor for glucosylceramidase, exploiting the generated information on the features of the enzyme.

It was conceived that the desired potent and specific inhibitor for the glucosylceramidase should have the following features:

1—a deoxynijirimycin-moiety;
  a proven, relatively potent inhibitor of the enzymatic activity of glucosylceramidase.

2—a N-alkyl spacer;
  N-alkylation of deoxynojirimycin was found to increase its capacity to inhibit glucosylceramidase.

3—coupled to the spacer a large hydrophobic group that tends to insert in a lipid bilayer, preferably (invaginations of) the plasma membrane;
  preferential insertion of the inhibitor in glucosylceramidase-containing membranes should increase the in vivo capacity and specificity of the inhibitor.

SYNTHESIS OF DEOXYNOJIRIMYCIN-ANALOGUES

Figure 1:
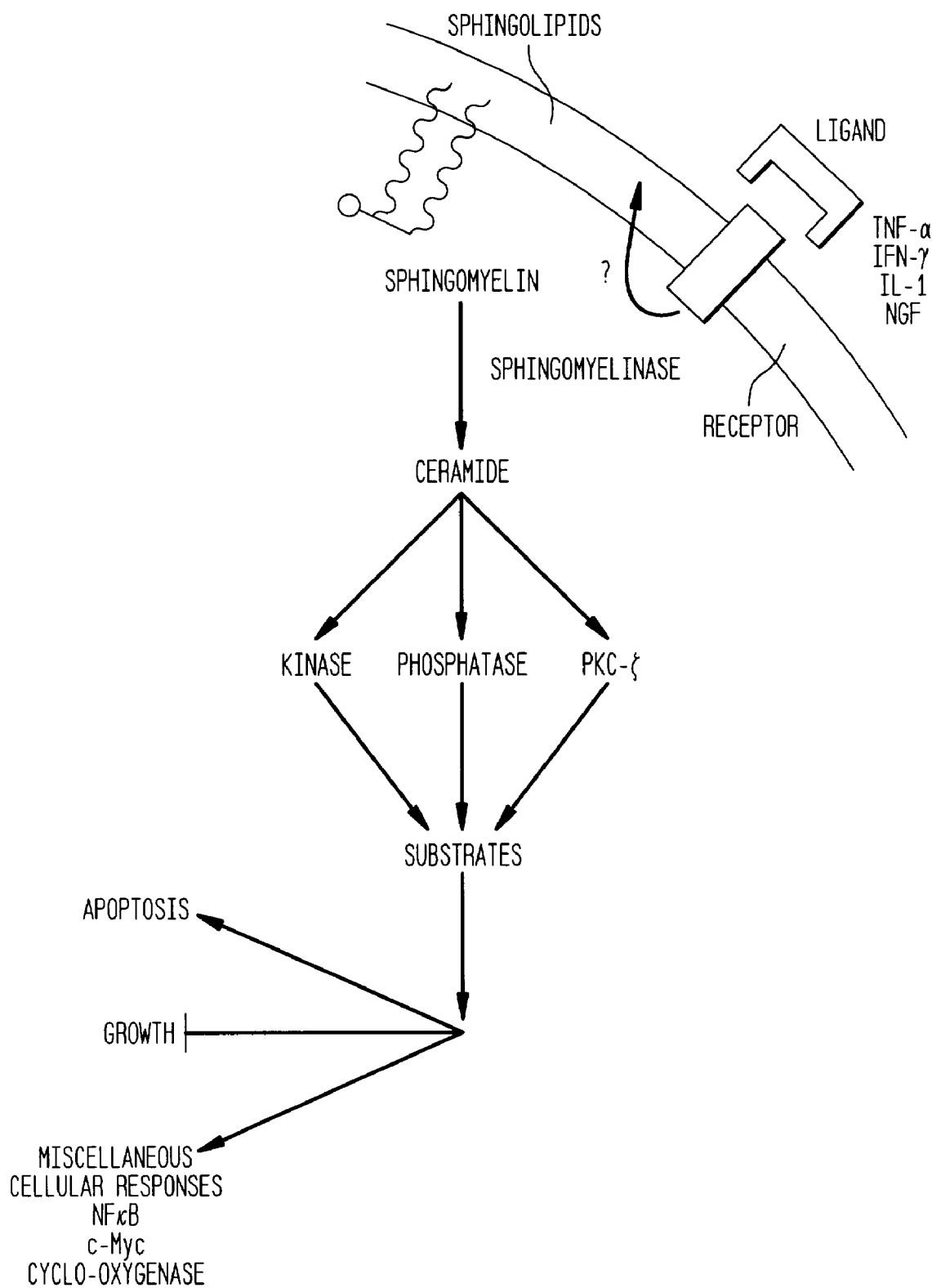
FIG. 1 presents a schematic overview of signalling through ceramide. TNF-α (tumor necrosis factor alfa), IL-1 (interleukin 1), NGF (nerve growth factor), IFN (interferon gamma) bind to their receptors, whereupon a neutral sphingomyelinase generates ceramide from sphingomyelin. Ceramide activates protein kinases and phosphatase which results in a cellular response.
Figure 2:
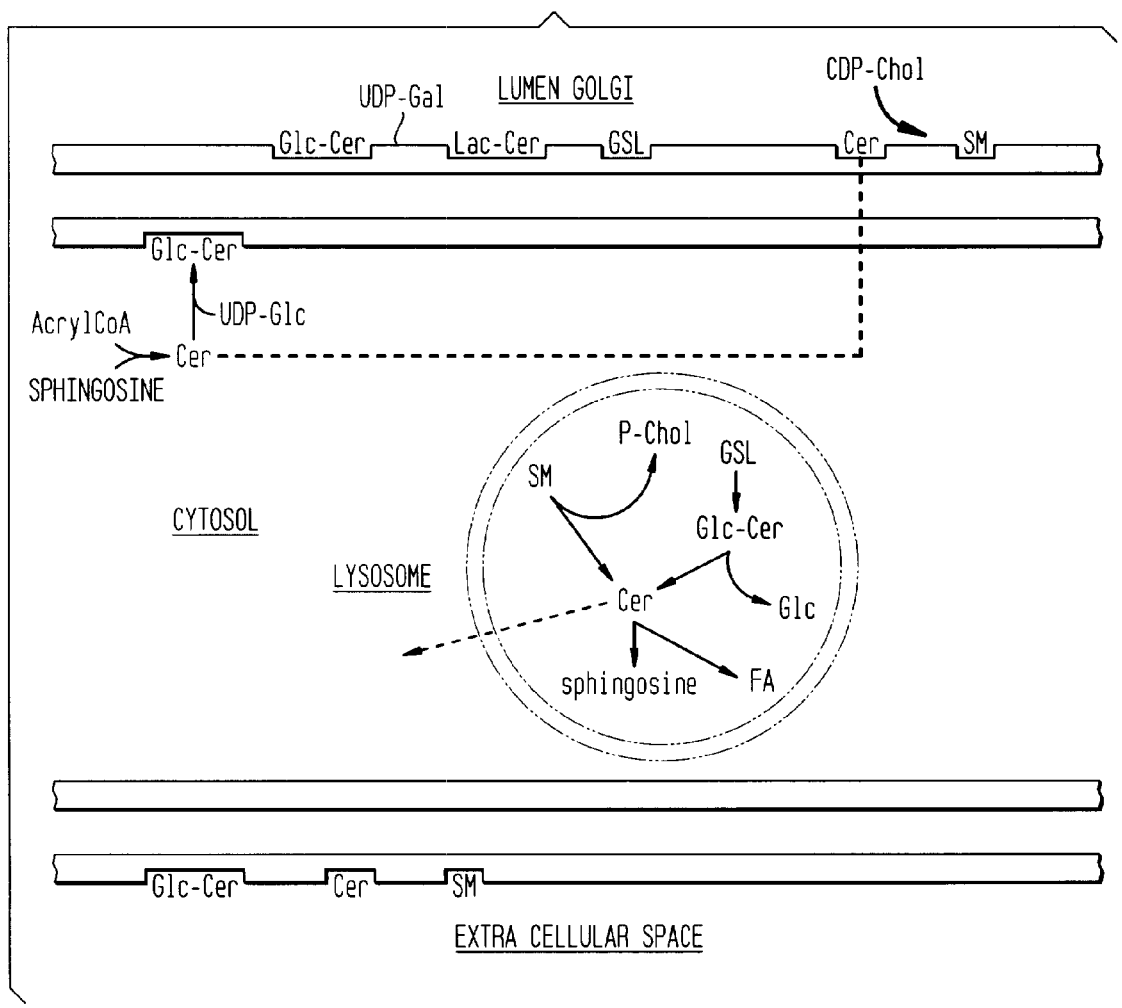
FIG. 2 presents a schematic overview of metabolism of ceramide. Abbreviations used therein: Chol=choline; Glc=glucose; GlcCer=glucosylceramide; GSL=complex glycosphingolipid; LacCer=lactosylceramide; SM=sphingomyelin.

A series of deoxynojirimycin-derivatives was made by chemical synthesis in order to test the concept and develop the ideal inhibitor for the glucosylceramidase. Based on the abovementioned features, a series of deoxynojirimycin (DNM) derivatives of the following type were synthesized (FIG. 1):

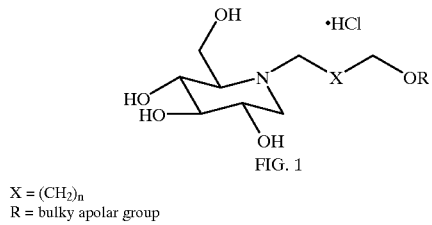

FIG. 1

X = (CH$_2$)$_n$
R = bulky apolar group

In this structure, X is a saturated alkane chain and R is a large apolar group. Compounds of this type can be synthesized by reacting DNM.HCl, which is readily available in seven steps from the commercially available tertabenzyl-glucopyranose [18], with the appropriate aldehyde, in a reductive amination [19] reaction (scheme 1).

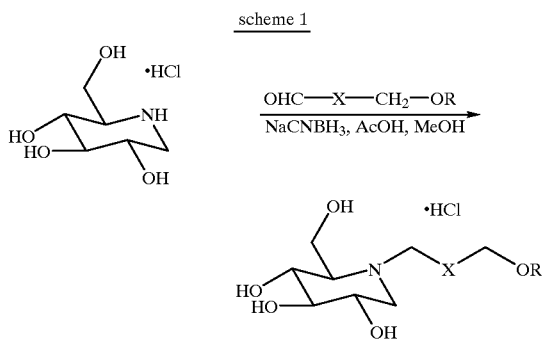

scheme 1

The strategy is exemplified by the synthesis of the following two compounds: N-(5-cholesteroloxy-pentyl)-deoxynojirimycin 9 and N-(5-adamantane-1-yl-methoxy-pentyl)-deoxynojirimycin 10 (scheme 2). Thus, glutaric aldehyde 1 was first converted into the monoacetal 2 [20] using an ion exchange catalyst. After reduction of the monoacetal to the corresponding alcohol 3 and transformation to the mesviate 4, reaction with the appropriate alcohol, in which ROH is cholesterol and adamantanemethanol respectively, under basic conditions, afforded the acetals 5 and 6. After liberation of the second aldehyde function, that is formation of compounds 7 and 8, reductive amination with DNM.HCl afforded the target compounds 9 and 10.

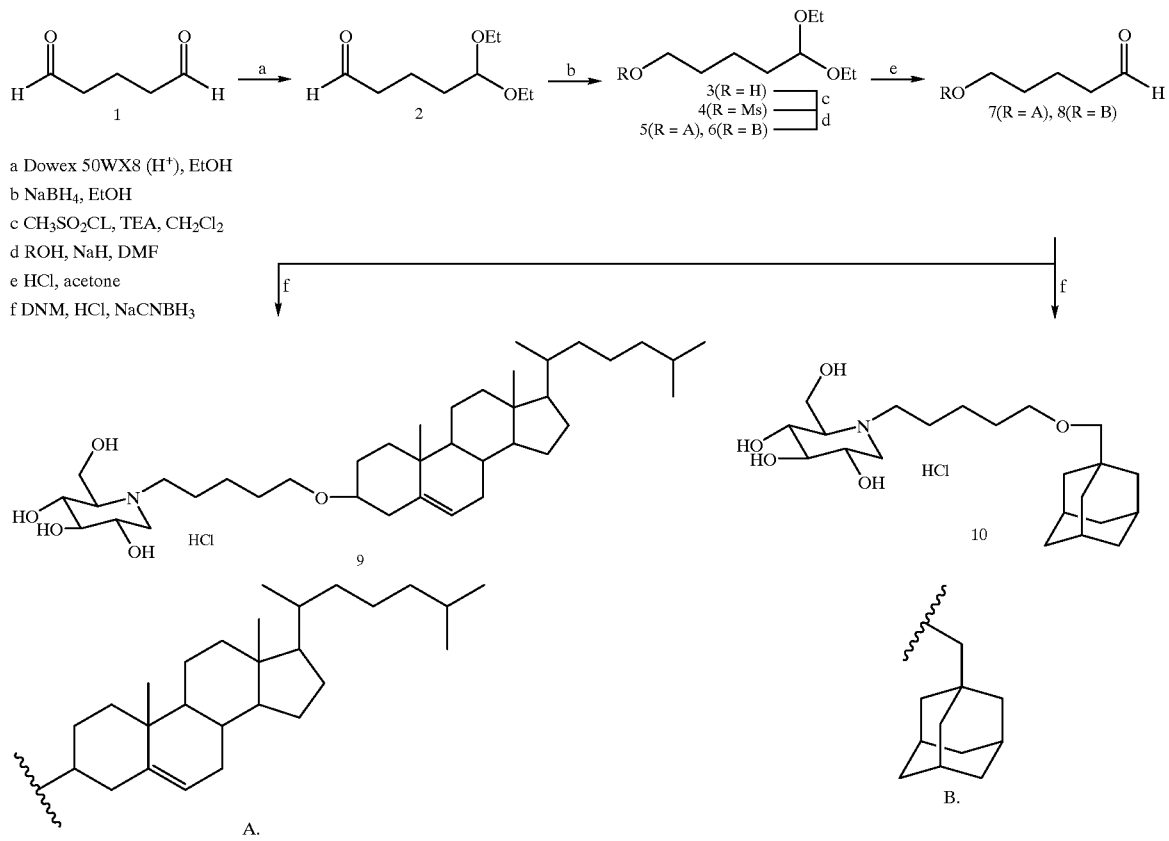

scheme 2 a Dowex 50WX8 (H$^+$), EtOH
b NaBH$_4$, EtOH
c CH$_3$SO$_2$CL, TEA, CH$_2$Cl$_2$
d ROH, NaH, DMF
e HCl, acetone
f DNM, HCl, NaCNBH$_3$

QUANTIFICATION OF THE INHIBITORY EFFECTS OF DEOXYNOJIRIMYCIN-ANALOGUES

The inhibitory effects of the various deoxynojirimycin-analogues on relevant enzyme activities were analysed in vitro and in intact cells.

IN VITRO EXPERIMENTS

Firstly, in vitro experiments were performed with purified human enzymes and membrane suspensions of human tissue. Attention was focussed to the inhibition of lysosomal glucocerebrosidase and glucosylceramidase activities and that of the lysosomal a-glucosidase. As source for glucosylceramidase were used a membrane fraction from human spleen. The glucosylceramidase activity was measured as the hydrolytic activity towards 4MU-b-glucoside in the membrane suspension that was pre-treated with conduritol B-epoxide to abolish the activity of glucocerebrosidase. As source of glucocerebrosidase served human placental enzyme (Ceredase, Genzyme Corp. Boston,USA) that is used in enzyme therapy. Alternatively, glucocerebrosidase activity was determined in a membrane fraction from human spleen. Glucocerebrosidase activity was measured as the hydrolysis of 4MU-b-glucoside that is inhibitable by conduritol B-epoxide. Lysosomal a-glucosidase activity was measured as the hydrolytic activity towards 4MU-a-glucosidase shown by a purified a-glucosidase preparation.

Tables 6 and 7 show the structures of the tested compounds. Table 3 gives an overview of the apparent Ki values of the inhibitors.

It can be seen in Table 3 that glucosylceramidase is potently inhibited by N-alkyl derivatives of deoxynojirimycin. Optimal inhibition was noted for the N-pentyl derivative. N-hexyl-deoxynojirimycin was a less potent inhibitor (not shown in Table 3). The presence of a carbonyl moiety in the spacer negatively influences the inhibitory capacity.

Coupling of a large hydrophobic group such as adamantane P21) or cholesterol (P24) to a N-pentyl spacer dramatically increases the capacity of the compound to inhibit the glucosylceramidase activity.

IC50 values were also determined in the case of some inhibitors. The apparent IC50 values for P21 and P24 are extremely low, 1 nM and 0.1 uM, respectively. For a comparison, the IC50 values for deoxynojirimycin and butyl-deoxynojirimycin are 20 uM and 0.3 uM, respectively.

Table 3 shows that glucocerebrosidase is in general less sensitive to deoxynojirimycin derivatives than glucosylceramidase.

Pure glucocerebrosidase in solution (Ceredase) and enzyme associated to membranes show a different sensitivity for the inhibitors. Apparently, the kinetic properties of the enzyme in these two different states differ, as is also suggested by the difference in apparent Km for 4MU-b-glucoside.

Both the soluble and membrane-associated glucocerebrosidase are most potently inhibited by deoxynojirimycin-analogues with a N-pentyl spacer and coupled to it a large hydrophobic group.

For soluble glucocerebrosidase (Ceredase) the apparent ICS50 value of P21 was 0.2 uM, and that of P24 was 0.8 uM; for the membrane-associated glucocerebrosidase the apparent IC50 values of P21 and P24 were 0.06 and 0.7 uM, resp.

With respect to the lysosomal a-glucosidase it was found that substitutions in deoxynojirimycin generally exerted relatively little effect. However, the compounds P4, P11, P16, P9 and P13 were very poor inhibitors.

IN VIVO EXPERIMENTS

Next, the capacity of the deoxynojirimycin-analogues to inhibit the glucosylceramidase and the glucocerebrosidase activities in intact cells was investigated. Enzyme activities were measured as described in ref. 17. Briefly, the hydrolysis of 4MU-b-glucoside by cultured melanoma cells that were pre-incubated with and without conduritol B-epoxide was determined. The conduritol B-epoxide sensitive activity can be ascribed to glucocerebrosidase and the insensitive activity to glucosylceramidase. The results of this study are shown in Table 4.

A comparison of Table 3 and Table 4 reveals that the inhibition by deoxynojirimycin analogues of the glucosylceramidase activity in intact melanoma cells is similar to that observed in in vitro experiments using splenic membrane preparations. The most potent inhibitors are P21 and P24 with IC50 values of about 0.3 nM and 50 nM. At these or ten-fold higher concentrations no significant inhibition of the glucocerebrosidase activity is detectable, see Table 4.

The inhibitory constants of deoxynojirimycin analogues were also determined by analysis of the metabolism of C6-NBD glucosylceramide in melanoma cells, employing again conduritol B-epoxide to discriminate between the activities of the insensitive glucosylceramidase and the sensitive glucocerebrosidase. The results obtained with C6-NBD glucosylceramide as substrate were almost identical to those obtained with the fluorogenic 4MU-b-glucoside substrate (not shown).

It was studied to which extent other reactions were inhibited by incubating cells with P21 or P24 at their IC50 concentration for the glucosylceramidase activity. Under these conditions no inhibition of glycogen synthase was noted in rat hepatocytes; no inhibition of glucosylceramide synthase activity or lysosomal a-glucosidase was noted in cultured melanoma cells.

Because of the extreme sensitivity of the glucosylceramidase for P21, it was examined whether the inhibition by this compound might be not reversible. To test this, melanoma cells were preincubated with or without P21, and subsequently washed extensively. Next, the glucocerebrosidase and glucosylceramidase activities were determined with 4MU-b-glucoside as substrate. It was found that the pretreatment with inhibitor was without significant effect on the glucocerebrosidase activity, but led to an irreversible loss of the glucosylceramidase activity.

PROOF OF CONCEPT: VALUE OF DEOXYNOJIRIMYCIN ANALOGUES FOR INTERVENTION IN MACROPHAGE ACTIVATION

The effect of P21 (N-(5-adamantane-1-yl-methoxypentyl) deoxynojirimycin) and butyldeoxynojirimycin on macrophages in culture was examined. The iminosugars, dissolved in DMSO at a concentration of 10 mM, were added to cultured macrophages at various concentrations by dilution in culture medium. It was checked that the minor amounts of DMSO introduced in this manner were without effect.

Table 5 shows the inhibition by the deoxynojirimycin analogues of the glucocerebrosidase and glucosylceramidase activities in macrophages, as measured with C6-NBD glucosylceramide as substrate; the effects are quite comparable to those noted for the enzymes in melanoma cells. Table 5 shows furthermore the effect of the deoxynojirimycin analoguess on the secretion of chitotriosidase by the cells. It can be seen that chitotriosidase secretion is reduced concomitantly with inhibition of the activity of glucosylceramidase, but not of that of the lysosomal glucocerebrosidase. Using C6-NBD ceramide as substrate, glucosylceramide synthase activity in cultured macrophages was also determined. It was noted that this enzyme activity is not significantly inhibited by the presence of 5 uM butyldeoxynojirimycin in the culture medium, a condition causing a reduced chitotriosidase secretion. Moreover it was found that inhibition of glucosylceramide synthase by the presence of PDMP or PPMP was without effect on chitotriosidase secretion.

In conclusion, the experiments show that low concentrations of butyldeoxynojirmycin and particularly of P21 are able, by virtue of their specific inhibition of glucosylceramidase activity, to de-activate macrophages that massively secrete chitotriosidase (and concomitantly other hydrolases and cytokines). Thus, experimental proof of concept has been obtained.

APPLICATIONS OF THE INHIBITORS OF GLUCOSYLCERAMIDASE ACTIVITY

One application for the newly developed, highly specific inhibitors is to be found in therapeutic intervention of Gaucher disease. As discussed above, the effects of the inhibitors on macrophage activation may be expected to favourably interfere with the pathogenesis of Gaucher disease. The administration of inhibitors may improve the efficacy of enzyme therapy, and consequently result in an improved clinical response and a marked reduction of associated costs.

A beneficial effect might also be exerted by inhibitors of glucosylceramidase activity in the case of other disease states that are characterized by elevated plasma chitotriosidase, such as the Niemann-Pick disease and sarcoidosis [4,5]. Furthermore it is known to us that foam cells in atherosclerosis are over-producing chitotriosidase.

It is likely that ceramide-mediated signalling processes are directly or indirectly effected by inhibition of glucosylceramidase activity. The potential applications for the developed inhibitors can therefore be extremely diverse. Of particular interest are inflammatory states that are provoked by TNF-α or other proinflammatory cytokines that signal through ceramide. Examples in this connection are septic shock, rheumatoid arthritis and Crohn's disease.

The selection of a suitable route of administration and suitable formulations of pharmaceutical compositions is within the normal skills of the persons skilled in the art. Examples of suitable administration routes are parenteral (intravenous, subcutaneous, intramuscular) injections or infusions, oral ingestion, and topical application. In particular attractive is the use of oily vehicles allowing slow and sustained release from the repository preparation. The use of an oily vehicle will not be feasible in the case of oral ingestion or intravenous administration. In the case of oral ingestion, absorption of the lipophilic compound will occur spontaneously in the gastro-intestinal tract upon the solubilization of the compound in mixed micelles followed by passive diffusion across the enterocyte membrane. In the case of intravenous administration use can be made of liposomes in which the lipophilic compound has prior been incorporated.

EXPERIMENTAL 5,5-Diethoxy-pentan-1-ol 3

A mixture of 5,5-diethoxy-pentanal 1 (3 g, 17 mmol) and $NaBH_4$ (0.65 g, 17 mmol) in 30 ml EtOH was stirred at room temperature for 3 h. The solvent was evaporated and the residue was triturated with 10% NaOH and extracted with $CH_2Cl_2$. The organic layers were collected, dried ($Na_2SO_4$) and the solvent evaporated to give 2 purified by silica gel flash chromatography eluting with petroleum ether 60–80/ethyl acetate 1:1 (yield 59%).

1H NMR ($CDCl_3$): d 4.47 (t, 1H, J=5.7 Hz, C-1), 3.70–3.58 (m, 4H, C-5, $CH_2$ acetal), 3.46 (dq, 2H, J=7.1 Hz, 2.3 Hz, $CH_2$ acetal), 1.65–1.50 (m, 4H, C-2, C-4), 1.41 (m, 2H, C-3), 1.18 (t, 6H, J=7.1 Hz, $CH_3$ acetal).

Methanesulfonic acid 5,5-diethoxy-pentyl ester 4

To an ice cooled solution of 2 (0.3 g, 1.7 mmol) and triethylamine (0.21 g, 2.0 mmol) in 3 ml $CH_2Cl_2$, methanesulfonyl chloride (0.21 g, 1.9 mmol) was added. After stirring for 1 h at rt the mixture was washed with water and the solvent, dried on $Na_2SO_4$, evaporated in vacuo to give 4 (0.43 g, 1.7 mmol, 100%), which was used for the subsequent reaction without further purification.

1H NMR ($CDCl_3$): d 4.47 (dt, 1H, J=5.5 Hz, 2.5 Hz, C-1), 4.21 (dt, 2H, J=6.5 Hz, 2.7 Hz, C-5), 3.63 (m, 2H, $CH_2$ acetal), 3.48 (m, 2H, $CH_2$ acetal), 3.00 (s, 3H, $OSO_2CH_3$), 1.77 (m, 2H, C-2), 1.63 (m, 2H, C-4), 1.47 (m, 2H, C-3), 1.20 (t, 6H, J=7.0 Hz, $CH_3$ acetal).

1-(5,5-diethoxypentyloxymethyl)-adamantane 5

NaH (60% disp., 0.108 g, 2.7 mmol) was washed with pentane, and stirred with adamantanemethanol (0.3 g, 1.8 mmol) in 5 ml DMF, for 1h at rt yielding a suspension of the sodium salt. Compound 4 (0.4 g, 1.6 mmol) was added and the mixture was heated at 70° C. for 4 h and stirred at rt overnight. The mixture was treated with few drops of MeOH, poured into ice and extracted with diethyl ether (3×15 ml). The organic solvent, dried on $Na_2SO_4$, was evaporated and the residue purified by flash chromatography with petroleum ether 60–80/ethyl acetate 7:3 giving the desired compound 5 as a viscous syrup.

5: yield 34%. 1H NMR ($CDCl_3$): d 4.48 (t, 1H, J=5.7 Hz, C-1 chain), 3.61 (dq, 2H, J=7.1 Hz, 2.3 Hz, $CH_2$ acetal), 3.49 (dq, 2H, J=7.1 Hz, 2.2 Hz, $CH_2$ acetal), 3.37 (t, 2H, J=6.5 Hz, C-5 chain), 2.94 (s, 2H, $CH_2$ adamant.), 1.94 (m, 3H, adamant.), 1.73–1.51 (m, 16H, C-2, C-4 chain, adamant.), 1.45–1.35 (m, 2H, C-3 chain), 1.19 (t, 6H, J=7.1 Hz, $CH_3$ acetal).

1-(5,5-Diethoxy-pentyloxy)-17-(dimethylhexyl)-10,13-dimethyl-2,3,4,7,8,9,10,11,12,13,14,15,16,17-tetradecahydro-1H-cyclo-penta[a]phenanthrene (O-(5,5-diethoxypentyl)-cholesterol) 6

NaH (60% disp., 0.12 g, 3 mmol) was washed with pentane and heated with cholesterol (1.16 g, 3 mmol) in DMF (6 mL) at 65–70° C. during 45 min, yielding a suspension of the sodium salt. 5,5-diethoxy-O-methanesulfonylpentanol 4 (0.508 g, 2 mmol) was added and the mixture was heated at 70–75° C. during 20 h. The DMF was evaporated and the residue was extracted with ether and water. The ether extracts were dried ($Na_2SO_4$) and the residue after evaporation was purified by flash chromatography (PE 60/80—ethyl acetate 5/1) giving the product as a viscous syrup (0.63 g, 58%).

1H NMR ($CDCl_3$): d 5.31 (m, 1H, C-6 chol.), 4.45 (t, J=5.5 Hz, 1H, C-1 chain), 3.61 (dq, 2H, J=7.1 Hz, 2.4 Hz, $CH_2$ acetal), 3.45 (m, 4H, $CH_2$ acetal, C-5 chain), 3.10 (m, 1H, C-3 chol.), 2.34 (m, 1H, chol.), 2.16 (m, 1H, chol.), 2.07–1.70 (bm, 4H), 1.70–0.75 (bm, 46H, chol., $CH_3$ acetal), 0.67 (s, 3H, $CH_3$ chol.).

5-[17-(dimethylhexyl)-10,13-dimethyl-2,3,4,7,8,9,10,11,12,13,14,15,16,17-tetradecahydro-1H-cyclopenta(a)phenanthren-3-yl-oxy]-pentanal (5-cholesterylpentanal) 7

5-(adamantan-1-yl-methoxy)-pentanal 8

A mixture of the appropriate acetal 5, 6, (0.2 mmol) in 3 ml acetone and 1 ml 5% HCl was stirred at rt for 1h. Evaporation of the acetone, extraction of the residue with ether (3×7ml), drying on $Na_2SO_4$ and evaporation yielded the aldehyde (quant.) used for the next step without further purification.

7: yield 100%. 1H NMR ($CDCl_3$): d 9.77 (s, 1H, CHO), 5.33 (m, 1H, C-6 chol.), 3.46 (t, 2H, J=6.1 Hz, C-5 chain), 3.11 (m, 1H, C-3 chol.), 2.46 (dt, 2H, J=7.2 Hz, 1.4 Hz, C-2 chain) 2.34 (m, 1H, chol.), 2.16 (m, 1H, chol.), 2.05–1.75 (bm, 42H, C-3 C-4 chain, chol), 0.67 (s, 3H, $CH_3$ chol.).

8: yield 100%. 1H NMR (CDCl$_{13}$): d 9.76 (t, 1H, J=1.7 Hz, CHO), 3.38 (t, 2H, J=6.2 Hz, C-5 chain), 2.94 (s, 2H, CH$_2$ adamant.), 2.46 (dt, 2H, J=7.2 Hz, 1.7 Hz, C-2 chain), 1.95 (m, 3H, adamant.), 1.80–1.45 (m, 16H, C-3, C-4 chain, adamant.).

1-{5-[17-(dimethylhexyl)-10,13-dimethyl-2,3,4,7,8,9,10,11,12,13,14,15,16,17-tetradecahydro-1H-cyclopenta[a]phenanthren-3-yl-oxy]-pentyl}-2-hydroxymethyl-piperidine-3,4,5-triol (N-(5-cholesterylpentyl)-deoxynojirimycin 9

The aldehyde 7 (0.118 g, 0.25 mmol) was dissolved in a small amount of hot ethyl acetate, diluted with ethanol (about 4 ml) and added to a solution of DNM which was prepared by stirring DNJ.HCl (0.050 g, 0.2 mmol) and sodium acetate (0.020 g, 0.25 mmol) in methanol (0.4 ml) at rt for 1 h. NaCNBH$_3$ (0.016 g, 0.25 mmol) was added at 0° C. and the suspension was stirred vigorously at rt during 18 h, and finally at 60° C. for 1 h. After cooling to rt the mixture was acidified (pH<1) with HCl (5%), stirred during 1 h and evaporated to dryness in vacuo. The remaining solids were suspended in a mixture of CH$_2$Cl$_2$ and methanol (1/1, 20 ml) and methanolic ammonia (20%, 2 ml) was added followed by silica (about 5 g). The mixture was (carefully) evaporated in vacuo to a free flowing solid, which was applied to a column of silica, pretreated with the eluent: CH$_2$Cl$_2$/MeOH/NH$_3$ in MeOH (20%)=80/15/5. The column was eluted with 80/15/5, 75/20/5 and 70/25/5 mixtures of this eluent, resp., yielding pure 9 (solid, 0.081 g, 0.13 mmol, 65%) after evaporation. Hydrochloride: compound 9 (0.050 g) was dissolved in hot ethanol (20–30 ml) and treated with 3 drops of conc. HCl. Evaporation of the solvents yielded the hydrochloride as a crystalline solid (quant.), mp 235–238° C. (sublimates from ca 190° C.).

1H NMR (D$_2$O): d 5.36 (m, 1H, C-6 chol.), 4.10 (d, 1H, J=12.6 Hz, C-6 DNM), 3.92 (d, 1H, J=12.6 Hz, C-6 DNM), 3.73 (m, 1H, C-2 DNJ), 3.61 (m, 1H, C-4 DNJ), 3.52 (t, 2H, J=6.2 Hz, C-5 chain), 3.47 (dd, JC-1/C-1=12.1, JC-1/C-2=4.8, C-1 eq.DNM), 3.39 (m, 2H, C-3 DNM, C-1 chain), 3.29–3.05 (m, 3H, C-1 chain, C-3 chol., C-5 DNM), 3.00 (app.t, 1H, J=11.6 Hz, C-1 ax. DNM), 2.34 (m, 1H, C-4 eq chol.), 2.15 (m, 1H, C-4 eq chol.), 2.03 (m, 1H, C-2 chol.), 1.97–0.80 (bm, 43H, C-2 C-4 C-3 chain, chol), 0.72 (s, 3H, CH$_3$ chol.). HRMS (FAB) obs mass 640.4979 (MNa$^+$), calcd for C$_{38}$H$_{67}$NO$_5$Na 640.4917; obs mass 618.5086 (MH$^+$), calcd for C$_{38}$H$_{68}$NO$_5$ 618.5097.

1-[5-adamantane-1-yl-methoxy)-pentyl]-2-hydroxymethyl-piperidine-3,4,5-triol (N-[5-adamantane-1-yl-methoxy)-pentyl]-deoxynojirimycin) 10

A solution of deoxynojirimycin hydrochloride (0.030 g, 0.15 mmol) and few µl of CH$_3$COOH in MeOH (2 ml) was added to 8 (0.056 g, 0.22 mmol) in MeOH (1 ml) at 0° C., followed by addition of NaCNBH$_3$ (0.014 g, 0.22 mmol). After stirring overnight at room temperature the reaction was concentrated, treated with 5% HCl (2 ml), stirred for 1 h at rt and solid Na$_2$CO$_3$ was added. The aqueous suspension was extracted with CH$_2$Cl$_2$ (3×7ml), the extracts combined, dried (Na$_2$SO$_4$) and evaporated in vacuo. The product was purified by silica gel flash chromatography (CH$_2$Cl$_2$/MeOH/8N NH$_3$ in MeOH 70:30:4), yielding pure 10 (0.030 g, 0.08 mmol, 50%). The resulting oil was dissolved in 5 ml MeOH and 1 ml 30% hydrochloric acid was added dropwise. The solvents and the excess of HCl were removed by coevaporation with methanol.

1H NMR (D$_2$O): d 4.11 (d, 1H, J=12.5 Hz, C-6 DNM), 3.98 (d, 1H, J=11.6 Hz, C-6 DNM), 3.82 (m, 1H, C-2 DNM), 3.69 (t, 1H, J=9.6 Hz, C-4 DNM), 3.62–3.45 (m, 4H, C-1 eq., C-3 DNM, C-5 chain), 3.36 (m, 1H, C-1 chain), 3.21 (m, 2H, C-5 DNM, C-1 chain), 3.08 (m, 3H, C-1 ax. DNM, CH$_2$ adamant.), 1.95 (m, 3H, adamant.), 1.90–1.56 (m, 10H, C-2, C-4 chain, adamant.), 1.52–1.30 (m, 8H, C-3 chain, adamant.). HRMS (FAB) obs mass 420.2745 (MNa$^+$), calcd for C$_{22}$H$_{39}$NO$_5$Na 420.2726; obs mass 398.2905 (MH$^+$), calcd for C$_{22}$H$_{40}$NO$_5$ 398.2906.

TABLE 1

OVERVIEW OF INHERITED SPHINGOLIPIDOSES IN MAN

| DISEASE | DEFECTIVE ENZYME |
|---|---|
| Sphingolipidoses | |
| GM1 gangliosidosis | β-galactosidase |
| GM2 gangliosidosis/Tay Sachs | hexosaminidase A |
| GM2 gangliosidosis/Sandhoff | hexosaminidase A and B |
| Galactosialidosis | protective protein |
| Ceramidetrihexoside lipidosis/Fabry | α-galactosidase |
| Metachromatic leukodystrophy | arylsulfatase A |
| Mucosulfatidosis | multiple sulfatase deficiency |
| Glucosylceramide lipidosis/Gaucher | glucocerebrosidase |
| Lipogranulomatosis/Farber | ceramidase |
| Sphingomyelin lipidosis/Niemann-Pick A/B | sphingomyelinase |
| Galactosylceramide lipidosis/Krabbe | galactocerebrosidase |
| α-N-acetylgalactosaminidase deficiency | α-N-acetylgalactosaminidase |

TABLE 2

CHITOTRIOSIDASE ACTIVITY IN PLASMA AND LEUKOCYTES
Chitotriosidase activity in plasma samples from control subjects, asymptomatic Gaucher disease patients, and symptomatic Gaucher disease patients was determined as described in ref. 4. Chitotriosidase deficient individuals are not included in the table.

| | PLASMA CHITOTRIOSIDASE (nmol/ml.h) | | |
|---|---|---|---|
| | CONTROLS | ASYMPTOMATICS | SYMPTOMATICS |
| mean | 22.4 | 98.4 | 16485 |
| n | 50 | 5 | 30 |
| range | 5.1–75.6 | 23.5–178.0 | 2949–55679 |

TABLE 3. APPARENT Ki VALUES OF VARIOUS GLYCOSIDASES

Ki values were determined by variation of substrate concentration at fixed inhibitor concentration and assuming competitive inhibition and Michaelis-Menten kinetics. All constants are expressed in uM. (–) implies that no inhibition was noted at an inhibitor concentration of 100 uM. The structures of the tested inhibitors are depicturted in Tables 6 and 7.

The activity of Ceredase towards 4MU-b-glucoside was determined in the presence of 0.25% (w/v) sodium taurocholate and 0.1% (v/v) Triton X-100 in citrate/phosphate buffer (pH 5.2). The activities of glucocerebrosidase and glucosylceramidase in membrane suspensions towards 4MU-b-glucoside were determined in citrate/phosphate buffer (pH 5.2). Conduritol B-epoxide was employed to discriminate between the two enzymes. The activity of lysosomal a-glucosidase towards 4MU-a-glucoside was determined in citrate/phosphate buffer at pH 4.0.

| INHIBITOR | GLUCOSYL-CERAMIDASE | GLUCOCEREBROSIDASE | | A-GLUCOSIDASE |
|---|---|---|---|---|
| | | CEREDASE | MEMBRANES | |
| DNJ | 28.8 | 506 | 141 | 1.46 |
| PROPYLDNJ | 0.123 | 546 | 332 | 9.24 |
| BUTYLDNJ | 0.31 | 912 | 424 | 6.43 |
| PENTYLDNJ | 0.038 | 249 | 8.5 | 3.74 |
| PENTANOYLDNJ | 84 | 670 | 83 | 2.39 |
| P4 | 461 | 19.7 | 3.2 | — |
| P11 | 306 | 113 | 4.1 | — |
| P16 | 39 | 11.6 | 0.44 | — |
| P9 | — | 51.6 | — | — |
| P13 | — | 11.2 | — | — |
| P21 | 0.0017 | 0.16 | 0.048 | 0.87 |
| P24 | 0.097 | 0.96 | 0.77 | 7.20 |
| Km (mM) | 3.28 | 3.25 | 1.45 | 1.88 |

Note:
Apparent IC50 values of P21 and P24 for soluble glucocerebrosidase (Ceredase) were 0.2 and 0.8 uM.
Apparent IC50 values of P21 and P24 for glucocerebrosidase in membrane suspension were 0.06 and 0.7 uM.
Apparent IC50 values of P21 and P24 for glucosylceramidase were 1 NM and 0.1 uM.

TABLE 4. IN VIVO INHIBITION BY DEOXYNOJIRIMYCIN ANALOGUES

Melanoma cells were incubated with various concentrations of inhibitors to determine their IC50 value (i.e. inhibitor concentration resulting in 50% inhibition). Activities of glucosylceramidase and glucocerebrosidase were determined as described in ref.17. NI=no significant inhibition detectable at 1 uM inhibitor.

| INHIBITOR | IC50 (nM) GLUCOSYL-CERAMIDASE | IC50 (nM) GLUCOCEREBROSIDASE |
|---|---|---|
| DNJ | 2000 | NI |
| PROPYLDNJ | 650 | NI |
| BUTYLDNJ | 200 | NI |
| PENTYLDNJ | 150 | NI |
| PENTANOYLDNJ | 30000 | NI |
| P4 | 200000 | 5000 |
| P11 | 200000 | 8000 |
| P16 | 20000 | NI |
| P21 | 0.3 | 100 |
| P24 | 50 | 800 |

TABLE 5. EFFECT OF DNJ ANALOGUES ON CULTURED MACROPHAGES

Human macrophages, obtained and cultured as described in ref. 4, were incubated with different concentrations butyldeoxynojirimycin (BDNJ) or N-5-adamantane-1-yl-methoxy-pentyl)deoxynojirimycin (P21). After 4 days pre-incubation with inhibitor, glucosylceramidase and glucocerebrosidase activities were determined with C6NBD-glucosylceramide as substrate [17] and at the same time the released chitotriosidase in the medium was determined [4]. Enzyme activities and chitotriosidase secretion in the presence of DNJs are related to those in the absence of inhibitor (100%).

| INHIBITOR | GLUCOSYL-CERAMIDASE ACTIVITY | GLUCOCEREBOSIDASE ACTIVITY | CHITOTRIOSIDASE SECRETION |
|---|---|---|---|
| NONE | 100 | 100 | 100 |
| B-DNJ 0.5 | 51 | 120 | 68 |
| (uM) 5 | 12 | 112 | 49 |
| 50 | 8 | 120 | 28 |
| P21 0.0025 | 90 | 120 | 105 |
| (nM) 0.05 | 65 | 115 | 72 |
| 1 | 40 | 130 | 64 |

Note: Glucosylceramide synthase activity is not significantly inhibited at 5 uM B-DNJ or 1 nM P21. The presence of PDMP or PPMP, while potently inhibiting glucosylceramide synthase activity, does not result in reduced chitotriosidase secretion.

TABLE 6

N-Alkyl deoxynojirimycin derivatives

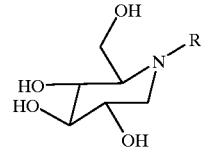

| | |
|---|---|
| DNJ | R = —H |
| N-propyl DNJ | R = —(CH$_2$)$_2$—CH$_3$ |
| N-butyl DNJ | R = —(CH$_2$)$_3$—CH$_3$ |
| N-pentyl DNJ | R = —(CH$_2$)$_4$—CH$_3$ |
| N-hexyl DNJ | R = —(CH$_2$)$_5$—CH$_3$ |
| N-pentanoyl DNJ | R = —CO—(CH$_2$)$_3$—CH$_3$ |

TABLE 7. N-Complex deoxynojirimycin derivatives (see next page)

Names of the large apolar groups: 1. adamantanemethanol; 2. adamantanol; 3. 9-hydroxy-phenanthrene; 4. cholesterol; 5. β-cholestanol; 6. adamantanemethanol; 7. cholesterol.

In structure 1–5 the large apolar groups are linked to DNJ by a chain bearing two carbonyl groups. These two groups are replaced by methylene groups in structure 6 and 7.

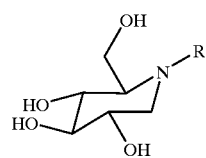

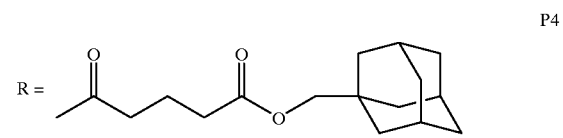

P4

-continued

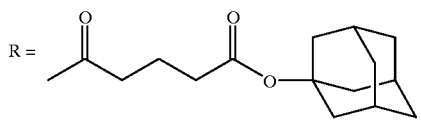
P11

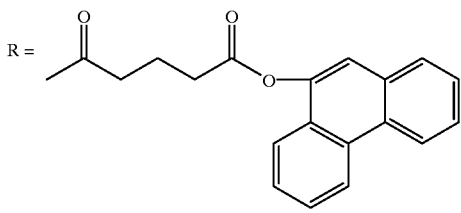
P16

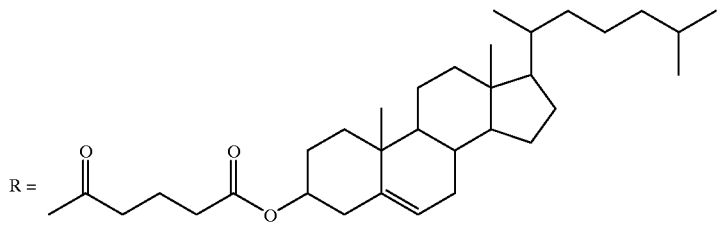
P9

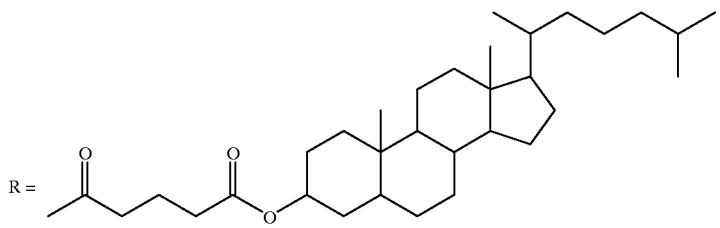
P13

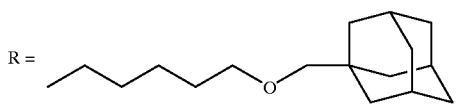
P21

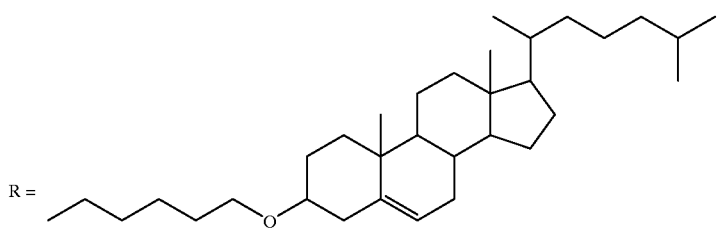
P24

REFERENCES

1. Heller, R. A., Kronke, M. (1994) J. Cell Biol. 126, 5–9. Tumor necrosis factor receptor-mediated signalling pathways.
2. Hannun, Y. A. (1994) J. Biol. Chem. 269, 3125–3128. The sphingomyelin cyclin and the second messenger function of ceramide.
3. Barranger, J. A., Ginns, E. I. (1989). Glucosylceramide lipidoses: Gaucher's disease. In: The Metabolic Basis of Inherited Diseases. C. R. Scriver, A. L. Beaudet, W. S. Sly & D. Valle, editors; McGraw-Hill Inc. New York, 1677–1698.
4. Hollak, C. E. M., van Weely, S., van Oers, M. H. J., Aerts, J. M. F. G. (1994) J. Clin. Invest. 93, 1288–1292. Marked elevation of plasma chitotriosidase activity. A novel hallmark of Gaucher disease.
5. Guo, Y., He, W., Boer, A. M., Wevers, R. A., de Bruyn, A. M., Groener, J. E. M., Hollak, C. E. M., Aerts, J. M. F. G., Galjaard, H., van Diggelen, O. P. (1995) J. Inher. Metab. Dis. 18, 717–722. Elevated plasma chitotriosidase activity in various lysosomal storage disorders.
6. Renkema, G. H., Boot, R. G., Muysers, A. O., Donker-Koopman, W. E., Aerts, J. M. F. G. (1995) J. Biol. Chem. 270, 2198–2202. Purification and characterization of human chitotriosidase, a novel member of the chitinase family of proteins.
7. Boot, R. G., Renkema, G. H., Strijland, A. H., van Zonneveld, A. J., Aerts, J. M. F. G. (1995) J. Biol. Chem. 270, 26252–26256. Cloning of a cDNA encoding chitotriosidase, a human chitinase produced by macrophages.
8. Barton, N. W., Furbish, F. S., Murray, G. J., Garfield, M., Brady, R. O. (1990) Proc. Natl. Acad. Sci. USA 87, 1913–1916. Therapeutic response to intravenous infusions of glucocerebrosidase in a patient with Gaucher disease.
9. Hollak, C. E. M., Aerts, J. M. F. G., Goudsmit, R., Phoa, S. S. K. S., Ek, M., van Weely, S., von dem Borne, A. E. G. Kr., van Oers, M. H. J. (1995) Lancet 345, 1474–1478. Individualised low-dose alglucerase therapy for type 1 Gaucher's disease.
10. Grabowski, G. A., Barton, N. W., Pastores, G., Dambrosia, J. M., Banerjee, T. K., McKee, M. A., Parker, C., Schiffmann, R., Hill, S. C., Brady, R. O. (1995) Ann. Int. Medicine 122, 33–39. Enzyme therapy in type 1 Gaucher disease: comparative efficacy of mannose-terminated glucocerebrosidase from natural and recombinant sources.
11. Aerts, J. M. F. G., Boot, R. G., Renkema, G. H., van Weely, S., Jones, S., Hollak, C. E. M., van Oers, M. H. J. (1995) Sem. Hematol. 32, suppl. 1, 10–13. Molecular and biochemical abnormalities of Gaucher disease: chitotriosidase, a newly identified biochemical marker.
12. NIH Technology Assessment Panel on Gaucher Disease (1996) JAMA 275, 548–553. Gaucher disease. Current issues in diagnosis and treatment.
13. Marshall, E. (1995) Science 269, 1050–1055. Gene therapy's growing pains.
14. Abe, A., Radin, N. S., Shayman, J. A. (1996) Biochim. Biophys. Acta 1299, 333–341. Induction of glucosylceramide synthase by synthase inhibitors and ceramide.
15. Platt, F. M., Neises, G. R., Dwek, R. A., Butters, T. D. (1994) J. Biol. Chem. 269, 8362–8365. N-butyldeoxynojirimycin is a novel inhibitor of glycolipid biosynthesis.
16. Platt, F. M., Neises, G. R., Karlsson, G. B.,Dwek, R. A., Butters, T. D. (1994) J. Biol. Chem. 269, 27108–27114. N-butyldeoxygalactonojirimycin inhibits glycolipid biosynthesis but does not affect N-linked oligosaccharide processing.
17. van Weely, S., Brandsma, M., Strijland, A., Tager, J. M., Aerts, J. M. F. G. (1993) Biochim. Biophys. Acta 1181, 53–62. Demonstration of the existence of a second, non-lysosomal glucocerebrosidase that is not deficient in Gaucher disease.
18. Overkleeft, H. S., van Wiltenburg, J., Pandit, U. K. (1994) Tetrahedron 34, 4215–4224.
19. Baxter, E. W., Reitz, A. B. (1994) J. Org. Chem. 59, 3175–3185.
20. Wanner, M. J., Koomen, G. J. (1995) J. Org. Chem. 60, 5634–5637.

What is claimed is:

1. Deoxynojirimycin compound containing a hydrophobic moiety linked through a spacer to the nitrogen atom of deoxynojirimycin, and salts thereof, wherein the spacer comprises an alkoxy polyalkylene or polyalkylene chain of from 3 to 8 carbon atoms and the hydrophobic moiety is a polycyclic alcohol group containing three or more rings that each share two or more carbon atoms with another ring and is capable of inserting in lipid bilayers.

2. A deoxynojirimycin compound according to claim 1 wherein the spacer comprises a polyalkylene chain of from 3 to 6 carbon atoms.

3. A deoxynojirimycin compound according to claim 1 wherein the spacer is a group having the structure —$(CH_2)_n$— wherein n is an integer from 3 to 8.

4. A deoxynojirimycin compound according to claim 1 wherein the hydrophobic moiety is derived from adamantanementhanol, cholesterol, β-cholestanol, or 9-hydroxyphenanthrene.

5. A deoxynojirimycin compound according to claim 2 wherein the spacer is a polyalkylene chain having 5 carbon atoms.

6. Pharmaceutical composition comprising a deoxynojirimycin compound according to claim 1 and a pharmaceutically acceptable carrier.

7. A method of treatment of an individual suffering from Gaucher Fabry, Tay Sachs, Sandhoff or Niemann-Pick diseases, comprising administering to said individual an effective amount of a deoxynojirimycin derivative according to claim 1, optionally in combination with an effective amount of native or recombinant, modified or unmodified glucocerebrosidase.

* * * * *